United States Patent [19]

Loewe et al.

[11] 4,117,156
[45] Sep. 26, 1978

[54] ANTHELMINTIC PREPARATIONS

[75] Inventors: Werner Loewe, Zurich; Heini Paul Striebel, Basel, both of Switzerland

[73] Assignee: Ciba-Geigy AG, Basle, Switzerland

[21] Appl. No.: 768,804

[22] Filed: Feb. 15, 1977

Related U.S. Application Data

[63] Continuation-in-part of Ser. No. 704,899, Jul. 13, 1976, abandoned.

[30] Foreign Application Priority Data

Jul. 18, 1975 [CH] Switzerland .................. 9438/75

[51] Int. Cl.$^2$ ............................................. A01N 9/18
[52] U.S. Cl. ................................................. 424/302
[58] Field of Search ......................................... 424/302

[56] References Cited

U.S. PATENT DOCUMENTS 3,755,406  8/1973  Brenneisen et al. ............ 424/302 X

FOREIGN PATENT DOCUMENTS

66/7298  4/1967  South Africa.

*Primary Examiner*—Allen J. Robinson
*Attorney, Agent, or Firm*—Theodore O. Groeger; John J. Maitner

[57] ABSTRACT

The present invention relates to anthelmintic preparations containing 4-(4-nitroanilino)-phenylisothiocyanate having a median of particle size of at most 10 μm, particularly at most 5 μm, and to the treatment of infections by parasitic helminthes, especially to the treatment of warm-blooded animals affected by shistosomiasis, hookworm infestation of filariasis, by administration of the preparations named above. Specific embodiments are suspensions of the active substance in triglycerides of medium saturated fatty acids, and mixtures of the active substance with a starch, particularly with maize starch.

18 Claims, No Drawings

ANTHELMINTIC PREPARATIONS

This is a continuation-in-part of our copending application Ser. No. 704,899 filed July 13, 1976 now abandoned.

The present invention relates to anthelmintic preparations containing 4-(4-nitroanilino)-phenylisothiocyanate.

It is known that 4-(4-nitroanilino)-phenylisothiocyanate has anthelmintic activity: see, for example, the American Patent Specification No. 3,755,406 and corresponding patent specifications of other countries. Nematodes, inter alia Strongylidae and Ancylostomatidae, as well as Cestoda and Trematoda such as Fasciolidae, are mentioned as being classes of worms that can be combatted with the substance mentioned. In test examples there are given, inter alia, the favourable results of tests on mice infested with Hymenolepis nana (dwarf tapeworm) as well as on rats infested with Fasciola hepatica (liver fluke); that is, therefore, favourable results also with regard to combatting helminthes, which are of importance from the point of view not only of veterinary medicine but also of human medicine.

It has now been found that particularly in the combatting of helminthes, which are important in human medicine, in the intestinal tract, such as hookworm (especially Ancylostoma or Necator), and particularly in the blood stream, such as Schistosoma (especially S. haematobium, S. mansoni and S. japonicum), by means of 4-(4-nitroanilino)-phenylisothiocyanate a degree of fineness of the 4-(4-nitroanilino)-phenylisothiocyanate (m.p. 204°–206° C) that is unattainable with normal grinding is of great importance for obtaining a strong and reliable anthelmintic action, and renders possible a surprisingly large reduction of the therapeutically necessary amount of active ingredient. In conformity with these findings, the present invention relates to anthelmintic preparations for oral or rectal administration to warm-blooded animals, which preparations contain an anthelmintically effective amount of 4-(4-nitroanilino)-phenylisothiocyanate in solid form having a median of particle size of at most 10 μm and preferably of at most 5 μm, together with pharmaceutical carrier substances. The active ingredient can be contained in solid preparations, such as in tablets, dragees, capsules or powders, for example as a mixture with other solid substances; or it can be contained in liquid or semi-solid preparations as a suspension, which may also be emulsified. Of particular importance are preparations which consist of the suspensions of the active ingredient in triglycerides of fatty acids or of mixtures of the active ingredients with starches, which are described hereinafter, or preparations which contain such suspensions or mixtures.

The particle size necessary according to the invention can be obtained with the aid of grinding processes known per se; the present invention is not limited in any way to the use of a specific type of mill, such as that mentioned hereinafter as an example, or even to the use of a specific make. A mean particle size of 10 μm, and optionally down to 5 μm, can be obtained for example by grinding the crystallised active ingredient in a jet mill, especially in a counter-jet mill. There may be mentioned, merely as examples of such mills, those of George W. Helme Co., Drost-jet Mill Division, Helmetta, New Jersey 08828, USA, see in this respect U.S. Pat. Specifications Nos. 2,704,635 and 3,229,918, as well as the journal "Chemieanlagen + Verfahren" (Chemical plant + Processes) 1970, Issue 7, pages 50–54. Still smaller particle sizes can be attained by wet grinding in stirrer ball mills, for example in water or in triglycerides of $C_8$–$C_{22}$ fatty acids such as in tri-glycerides of higher, i.e. $C_{14}$–$C_{22}$ fatty acids, and particularly in triglycerides of saturated medium i.e. $C_8$–$C_{14}$, especially $C_8$–$C_{12}$ fatty acids. As examples of such mills, there may be mentioned the Dyno ®-mills, protected trade-mark of W. A. Bachofen, CH-4005 Basle, see Chemische Rundschau 28 (1975), No. 10, pages 3–7; Experientia 27 (1971), No. 9, pages 1103–1104; Biotechnology and Bioengineering 15, (1973), 125–142 and 16 (1974), 623–634; as well as the Swiss Patent Specification No. 550,024.

The surprising increase in effectiveness as a result of the reduction of particle size according to the invention and optionally of further measures according to the invention is shown, for example, from the results of animal tests summarised below in Tables I, II and III. The preparations E, F, G and H according to the present invention were compared with the preparations A, B and C containing active substance with a higher particle size and with the solution D containing 5% of the active substance. The preparations tested were the following:

A. 1–3% Suspensions of 4-(4-nitroanilino)-phenylisothiocyanate of a median of the particle size of about 50 μm in aqueous isotonic sodium chloride solution containing 0.2% of TWEEN 80 (protected trademark of ICI United States Inc.).

B. 0.5–3% Suspensions of 4-(4-nitroanilino)-phenylisothiocyanate of a median of the particle size of 23,2 μm (in aqueous isotonic sodium chloride solution containing 0.2% of TWEEN 80.

C. Tablets containing 70% of 4-(4-nitroanilino)-phenylisothiocyanate of a median of the particle size of 23,2 μm.

D. 5% Solution of 4-(4-nitroanilino)-phenylisothiocyanate in liquid polyethylene-glycol of molecular weight 400.

E. 10 % Suspension of 4-(4-nitroanilino)-phenylisothiocyanate of a median of the particle size of 4,23 μm in aqueous isotonic sodium chloride solution containing 0,2% of TWEEN 80, prepared in a laboratory homogenizer, F. Tablets containing 70% of 4-(4-nitroanilino)-phenylisothiocyanate of a medium of the particle size of 4,23 μm prepared analogously to Example 3 given below with adaptation of the tablet size to test animals (dog and monkey).

G. 20% Suspension of 4-(4-nitroanilino)-phenylisothiocyanate of a medium of the particle size of 2 μm in triglycerides of $C_8$–$C_{12}$ saturated fatty acids = Migylol ® of Dynamit Nobel A.G., prepared according to Example 1 given below.

H. Mixture of 10% of 4-(4-nitroanilino)-phenylisothiocyanate of a median of particle size before mixing of 4,23 μm, with corn starch prepared according to Example 4 given below.

The test methods and results were as follows:

1. Anthelmintic activity in mice infested with Schistosoma mansoni and in hamsters infested with Schistosoma haematobium Adult white mice weighing 20–25 g were each infested with 80 cercariae of Schistosoma mansoni by subcutaneous injection. Eight weeks after infestation, different graduated single doses of the preparations to be tested were administered orally to groups of 10 mice except to a group of 20 mice serving as a control. Five weeks after this treatment, the mice were autopsied, the total of schistosomes present in each animal and each test group and in the control group was ascertained and therefrom the $ED_{50}$ (50% worm load reduction as compared with controls) and $ED_{90}$ (90% worm load reduction) of each preparation determined by the method of MILLER & TAINTER (1944) cp. MILLER, Lloyd C. & M. L. TAINTER, Estimation of the $ED_{50}$ and its Error by means of Logarithmic-Probit Graph Paper, Proc. Soc. Exp. Biol. Med., 57; 261–264. (1944).

The tests on hamsters infested with Schistosoma haematobium were carried out analogously with the following time intervals: 95 days between infestation with 200 cercariae and oral administration of the test preparation, 30 days between administration and evaluation.

were each simultaneously infested, by subcutaneous injection in the cervical region, with 600 cercariae of Schistosoma mansoni. The test animals were divided into 5 groups each of three, of which one group serves as a control group. The 4 remaining groups were used for testing two test preparations, preparation F and preparation H, each administered in two doses.

From the fifth week onward, the patency of the infestation was checked twice per week by means of the miracidia hatching test and when the excretion of eggs had become constant the animals were used for the test. The test preparations were administered 53 days after infestation with cercariae. The tablets F were administered directly per os; the mixture with corn starch H was administered as a suspension in the 9-fold amount of water containing 0.1% of TWEEN 80 (polyoxyethylenesorbitanmonooleate, protected trade-mark, ICI Table I

| Test No. | Parasite | Host | Preparation | | Median of particle size in μm | $ED_{50}$ mg/kg | $ED_{90}$ mg/kg |
|---|---|---|---|---|---|---|---|
| 1 | S.mansoni | mouse | A | (aqueous suspension) | 50 | 200 | 300 × 5* |
| 2 | S.mansoni | mouse | B | (aqueous suspension) | 23.2 | 37 | 180 |
| 3 | S.mansoni | mouse | C | (solution) | — | 25 | 100 |
| 4 | S.mansoni | mouse | D | (aqueous suspension) | 4.23 | 25 | 120 |
| 5 | S.mansoni | mouse | G | (suspension in triglyceride) | 2 | 9 | 25 |
| 6 | S.haematobium | hamster | A | (aqueous suspension) | 50 | 110 | not determined |
| 7 | S.haematobium | hamster | B | (aqueous suspension) | 23.2 | 43 | 90 |
| 8 | S.haematobium | hamster | G | (suspension in triglyceride) | 2 | <20 | 20 |

*Treatment on 5 successive days.

According to the results of the tests with mice shown in Table I, the $ED_{50}$ of the suspension in triglyceride G is about 4 times lower than that of the aqueous suspension of particle size 23,2 μm. When the particle size of the active substance in the aqueous suspension is reduced from 23.2 to 4.32 μm, the $ED_{50}$ and $ED_{90}$ become 1.5 time lower and are about equal to those of the solution in polyethyleneglycol C. Also on hamsters, the $ED_{50}$ and $ED_{90}$ of the suspension in triglycerides G are substantially lower than those of the aqueous suspension B.

2. Anthelmintic activity in green long-tailed monkeys infested with Schistosoma mansoni For the first test series fifteen adult green long-tailed monkeys (vervet monkey, Cercopithecus Aethiops), United States Inc., Wilmington DE 19897). After a further 30 days, the test animals were autopsied and the total number of male and female schistosomes present in the mesenteric vessels and portal system was determined by perfusion and careful inspection of all perfused mesenteric veins.

In the second test series, six test animals were each simultaneously infested with 2000 cercariae and, after the infestation had become patent with stable egg-excretion, the suspension G, filled into soft gelatine capsules, was administered to two test animals, with four animals serving as controls. After 30 days, the test animals were autopsied and the test evaluated as above.

Table II

| Preparation | Animal No. | Dose of active substance in mg/kg per os | Autopsy findings Number of Schistosoma | | | Reduction in % compared with corresp. controls | | |
|---|---|---|---|---|---|---|---|---|
| | | | male | female | total | of male | of female | or of all parasites |
| F tablet | 791 | 40 | 61 | 33 | 94 | 0 | 25 % | 0 |
| | 792 | 40 | 29 | 19 | 48 | | | |
| | 793 | 40 | 39 | 21 | 60 | | | |
| | 794 | 80 | 62 | 32 | 94 | 39 % | 46 % | 42 % |
| | 796 | 80 | 6 | 7 | 13 | | | |
| | 799 | 80 | 3 | 13 | 16 | | | |
| H mixture | 797 | 20 | 26 | 22 | 48 | 60 % | 73 % | 66 % |
| | 798 | 20 | 2 | 1 | 3 | | | |
| | 800 | 20 | 17 | 3 | 20 | | | |
| | 801 | 40 | 34 | 1 | 35 | 31 % | 91 % | 62 % |
| | 804 | 40 | 16 | 0 | 16 | | | |
| | 805 | 40 | 29 | 8 | 37 | | | |
| | 790 | Controls to F, H | 35 | 33 | 68 | | | |
| | 795 | | 36 | 32 | 68 | | | |
| | 803 | | 43 | 32 | 75 | | | |

Table II-continued

| Preparation | Animal No. | Dose of active substance in mg/kg per os | Autopsy findings Number of Schistosoma | | | Reduction in % compared with corresp. controls | | |
|---|---|---|---|---|---|---|---|---|
| | | | male | female | total | of male | of female | or of all parasites |
| G Suspension | 762 | 22.1 | 2 | 2 | 4 | 99,8 % | 99,7 % | 99,7 % |
| | 769 | 29.2 | 1 | 1 | 2 | | | |
| | 759 | Controls to G | 561 | 422 | 983 | | | |
| | 776 | | 537 | 464 | 1001 | | | |
| | 770 | | 888 | 675 | 1583 | | | |
| | 758 | | 499 | 358 | 857 | | | |

The best effect was obtained in this test with preparation G, the suspension in triglycerides of $C_8$-$C_{12}$ saturated fatty acids (particle size 2 μm), with a reduction of the number of parasites of more than 99%. The lower dosage, 20 mg/kg of preparation H, the mixture with corn starch, was more active than the fourfold dosage, 80 mg/kg of the tablets F.

(c) Anthelminthic action on beagle dogs infested with *Schistosoma mansoni*

Young beagle dogs weighing 5 to 7 kg were each percutaneously infested with 3000 cercariae of Schistosoma japonicum. When patency of infestation and stability of egg excretion, checked as in the preceding test, was attained, a single dose of a specific dosage of a preparation to be tested was administered orally to groups of 2 dogs, and two dogs in each test series served as controls. 35 to 44 days after administration of the test preparations the animals were autopsied and the number of parasites was determined as in the tests with monkeys.

When the active substance of the higher particle size is formulated as tablet C, the anthelminthic activity is superior to that of the aqueous suspension B, whereas the active substance of lower particle size is less active when it is administered in the form of the tablets F than it is in the form of aqueous suspension E. However, even in the less suitable form of tablets, 50 mg/kg of the active substance with a median of the particle size of 4,23 μm is already more active than 118-134 mg/kg of the active substance of higher particle size in the here more favourable tablet form, whereas 20 mg/kg of active substance of a median of the particle size of 4.23 μm administered in the form of an aqueous suspension is more active than 100 mg/kg of the active substance of higher particle size administered in the same way. Still much higher activity is shown by the mixture with corn starch H. In this preparation, 10 mg/kg of active substance is already as active as 117-134 mg/kg of active substance of higher particle size administered in the form of tablets, and 20 mg/kg of active substance in preparation H is more active than 50 mg/kg of active Table III

| Preparation (median of particle size in μm) | Animal No. | Dose of active substance in mg/kg per os | Autopsy findings Number of Schistosomes | | | Reduction in % compared with corresponding controls | | |
|---|---|---|---|---|---|---|---|---|
| | | | male | female | total | of male | of female | of all parasites |
| D (—, solution) | 3808 | 50 | 12 | 9 | 21 | 97.0 | 81.2 | 91.9 |
| | 3812 | 50 | 53 | 192 | 245 | | | |
| C (23.2) | 3802 | 134 | 101 | 76 | 207 | 92.3 | 90.7 | 91.7 |
| | 3806 | 118 | 43 | 23 | 66 | | | |
| B (23.2) | 4900 | 100 | 515 | 461 | 976 | 38.5 | 0 | 23.3 |
| | 4901 | 100 | 840 | 720 | 1560 | | | |
| | 3820 | Controls to D, C, B | 976 | 296 | 1272 | | | |
| | 4884 | | 1259 | 774 | 2033 | | | |
| F (4.23) | 552 | 20.8 | 629 | 446 | 1075 | 39 | 0 | 24.2 |
| | 553 | 20.1 | 1194 | 899 | 2093 | | | |
| | 4548 | 51 | 43 | 11 | 54 | 98.4 | 98.9 | 98.6 |
| | 4555 | 50 | 4 | 2 | 6 | | | |
| E (4.23) | 4551 | 20 | 289 | 208 | 497 | 90.3 | 81.5 | 87.8 |
| | 4544 | 20 | 0 | 13 | 13 | | | |
| H (4.23 before mixing) | 4554 | 10 | 40 | 2 | 42 | 93.5 | 91 | 92.8 |
| | 4547 | 10 | 154 | 106 | 260 | | | |
| | 4546 | 20 | 37 | 0 | 37 | 98.7 | 100 | 99.3 |
| | 4545 | 20 | 2 | 0 | 2 | | | |
| | 4542 | 40 | 23 | 6 | 29 | 99.2 | 99.5 | 99.3 |
| | 4543 | 40 | 0 | 0 | 0 | | | |
| | 4541 | Controls to F, E, H | 1050 | 233 | 1283 | | | |
| | 4549 | | 1935 | 963 | 2898 | | | |

On the basis of the test results given in Table III, the activities of two pairs, C vs F and B vs E, of otherwise identical preparations differing only with regard to the particle size of the active substance can be compared.

substance of lower particle size administered in the form of tablets F, and provides for a practically complete cure. Furthermore, it is of interest to note that, when the dosage of active substance is taken account of, the solution of the active substance D does not give better results than any of the preparations E, F and H containing solid active substance of low particle size according to the invention, and at least in the mixture with corn starch H the active substance is by far more potent than in the solution D which at first sight would be deemed to provide the best distribution and resorption of the active substance.

From the results given in the Tables I, II and III it is evident that all preparations containing the active substance 4-(4-nitroanilino)-phenylisothiocyanate with a median of the particle size of 4.23 μm or less according to this invention are more active against Schistosoma on mice, hamsters, and especially on green long-tailed monkeys and beagle dogs, than preparations containing the same active substance with a median of the particle size of 23.2 μm, and at least equally active as a solution of the said active substance in polyethylene glycol. Particularly remarkable is the increase of activity on green long-tailed monkeys against Schistosoma mansoni when active substance of a median of the particle size of 2 μm is administered in the form of a 20% suspension in triglycerides of $C_8$–$C_{12}$ saturated fatty acids, and on beagle dogs against Schistosoma japonicum when active substance of a median of particle size of 4.23 μm, before mixing, is administered in the form of a specifically prepared 10% mixture with corn starch.

The active ingredient of the particle size as defined can be processed with pharmaceutical carrier substances in a manner known per se, e.g. by means of conventional mixing, granulating, coating, suspending and encapsulating methods, into the customary preparations for oral or rectal administration. Thus, anthelmintic preparations for oral application can be obtained by combining the active ingredient of the defined particle size with solid pharmaceutical carriers; optionally granulating the resulting mixture; and processing the mixture or granulate, if desired and/or optionally after the addition of suitable auxiliaries, into the form of tablets or dragee cores.

Suitable pharmaceutical carriers for solid preparations are, in particular, fillers such as sugar, e.g. lactose, saccharose, mannitol or sorbitol, cellulose preparations and/or calcium phosphates, e.g. tricalcium phosphate or calcium hydrogen phosphate; also binding agents, such as starch paste, with the use, e.g., of maize, wheat, rice or potato starch, gelatine, tragacanth, methyl cellulose, hydroxypropyl-methyl cellulose, sodium carboxymethyl cellulose and/or polyvinylpyrrolidone, esters of polyacrylates or polymethacrylates with partially free functional groups; and/or, if required, effervescent agents, such as the above-mentioned starches, also carboxymethyl starch, cross-linked polyvinylpyrrolidone, agar, or alginic acid or a salt thereof, such as sodium alginate. Auxiliaries are primarily flow-regulating agents and lubricating agents, e.g. silicic acid, talcum, stearic acid or salts thereof, such as magnesium stearate or calcium stearate. Dragee cores are provided with suitable coatings, optionally resistant to gastric juices, whereby there are used, inter alia, concentrated sugar solutions optionally containing gum arabic, talcum, polyvinylpyrrolidone, and/or titanium dioxide, lacquer solutions in aqueous solvents or, for producing coatings resistant to stomach juices, solutions of esters of polyacrylates or polymethacrylates having partially free functional groups, or of suitable cellulose preparations such as acetylcellulose phthalate or hydroxypropylmethylcellulose phthalate, with or without suitable softeners such as phthalic acid ester or triacetin. Dyestuffs or pigments may be added to the tablets or dragee coatings, e.g. for identification or marking of the various doses of active ingredient.

Further anthelminthic preparations which can be administered orally are hard gelatine capsules, as well as hard or soft closed capsules made from gelatine and, if required, a softener such as glycerin or sorbitol. The hard gelatine capsules can contain the active ingredient in the form of a granulate, e.g. in admixture with fillers such as maize starch, optionally granulated wheat starch, binders or lubricants such as talcum, magnesium stearate or colloidal silicic acid, and optionally stabilisers. In closed capsules the active ingredient is in the form of a powder or granulate; or it is preferably present in the form of a suspension in triglycerides of fatty acids of higher or especially medium chain length, whereby for stabilising the suspensions there can be added, e.g., glycerin monostearate.

Other anthelmintic preparations to be administered orally are, for example, aqueous suspensions prepared in the usual manner, which suspensions contain the active ingredient in the suspended form and at a concentration rendering a single dose sufficient. The aqueous suspensions either contain at most small amounts of stabilisers and/or flavouring substances, for example sweetening agents such as saccharin-sodium, or as syrups contain a certain amount of sugar and/or sorbitol or similar substances. Also suitable are, for example, pulverulent concentrates or concentrated suspensions for the preparation of shakes. Such concentrates can also be packed in single-dose amounts.

Suitable anthelmintic preparations for rectal administration are, for example, suppositories consisting of a mixture of the active ingredient with a suppository foundation substance. Such substances are, in particular, natural or synthetic triglyceride mixtures. Also suitable are gelatine rectal capsules consisting of a suspension of the active ingredient in a foundation substance. Suitable foundation substances are, for example, liquid triglycerides, of higher or, in particular, medium saturated fatty acids.

Of particular importance among the above-mentioned preparations are those which contain the active ingredient as a suspension in an oily carrier substance, especially in triglycerides of $C_8$ to $C_{22}$ fatty acids, particularly of medium, i.e. $C_8$ to $C_{12}$, saturated fatty acids, as well as a small amount of a suspension stabiliser such as glycerin monostearate. There may be mentioned, merely as examples of corresponding triglycerides available commercially, Miglycol 812 and Miglyol 810, protected trade-marks of Dynamit Nobel A.G. for triglyceride mixtures of saturated fatty acids $C_8$–$C_{12}$ and $C_8$–$C_{10}$, respectively; as well as Myritol 318 and Sydermin GTC, protected trademarks for octanoic acid/-decanoic acid triglycerides of the series of Dehydag products of Henkel u. Co., G.m.b.H.. The triglycerides mentioned are very suitable as grinding liquids for wet grinding, and at the same time they facilitate also the absorption of the active ingredient in the intestines. By virtue of the last-mentioned property, the stated triglycerides are particularly advantageously used for producing preparations for combatting helminthes present in the blood stream, such as Schistosoma. The suspensions most suitable for grinding are those having a content of active ingredient of about 10 to 30%, preferably about 20%. A lower concentration of active ingredient desired for specific preparations can be obtained by subsequent addition of the natural or synthetic triglycerides mentioned or of others.

Likewise of particular interest are preparations containing the finely ground active ingredient, preferably that having a median of particle size of 5 μm or less, in admixture with a starch, especially with maize starch or wheat starch, also, for example, with potato starch or rice starch. Such admixtures preferably have a content of active ingredient of 5 to 20%, particularly 10%. They are produced preferably by means of a brief mixing in a high-speed mixer having a propeller-like, sharp-edged stirring device, for example with a mixing time of between 3 and 10 minutes, and in the case of larger amounts of constituents with cooling if necessary. In this mixing process, the particles of the active ingredient are uniformly deposited, with a continuing reduction of the size of some particles, onto the starch particles. The mixtures of the active ingredient with starches, especially the mixtures obtained in the aforesaid manner, are characterised, as seen from, inter alia, the described tests on the green long-tailed monkey, by a particularly high degree of effectiveness, which moreover is subject to less variation from one host animal to another. The mixtures mentioned can be processed with the customary, e.g. the aforementioned, auxiliaries into the form of solid dosage units; i.e., pressed for example into the form of tablets or dragees or filled into capsules. They can however also be used directly, or after the addition of auxiliaries, e.g. pharmaceutically acceptable wetting agents and distributing agents, such as esters of polyoxyethylene sorbitans with higher fatty acids or sodium lauryl sulphate, and/or flavouring substances, as concentrates for the preparation of aqueous suspensions, e.g. with the approx. 5- to 20-fold amount of water. Instead of combining the active ingredient/starch mixture with a surface-active substance or with other auxiliaries, these substances may also be added to the water used to prepare the suspension. The concentrates for producing suspensions, consisting of the active ingredient/starch mixtures and optionally auxiliaries, can be packed in single-dose amounts, if required in an airtight and moistureproof manner.

Anthelmintic preparation according to the invention contain the active ingredient at a concentration suitable for administration of the following doses to warm-blooded animals, which concentration is, depending on the mode of administration, between about 5% and 95%, preferably between about 10% and 90%. In the case of suspensions, the concentration is usually not higher than 30%, preferably about 20%; and conversely in the case of tablets, dragees and capsules with a pulverulent active ingredient the concentration is preferably not lower than about 40%, in order to ensure an easy ingestion of the required doses of active ingredient. Tablets, dragees and capsules having a pulverulent active ingredient contain 50 to 500 mg, preferably 100–250 mg, of active ingredient; and capsules filled with suspensions contain for example 50–300 mg, preferably 100–250 mg, of active ingredients.

The treatment of warm-blooded animals infested with parasitic helminthes with the preparations according to the invention is carried out preferably by a single oral or rectal administration of an amount which contains a dose of 4-(4-nitroanilino)-phenylisothiocyanate sufficient to practically completely free the warm-blooded animal from the parasitic helminthes, that is to say, an amount which is sufficient of cure said animal of the infection caused by the parasitic helminthes. If required, this curative dose can be divided into several partial doses which are administered at intervals of several hours, but all on the same day. The administered dose of the active ingredient, 4-(4-nitroanilino)-phenylisothiocyanate, is dependent both on the species and general condition of the warm-blooded animal to be treated and on the genus and species of the helminthes to be combatted, with their specific pattern of life and manner of reproduction, and if preferably between about 5 and 80 mg/kg, especially between about 5 and 30 mg/kg. For a fairly large warm-blooded animal of about 50–70 kg body weight for example, the dose to be administered is 250 to 2100 mg.

4-(4-Nitroanilino)-phenylisothiocyanate is effective, with very good compatibility, e.g. in experimental animals such as the mouse, rat, hamster, Mongolian Jird (Meriones unguiculatus), dog, monkey or fowl, against nematodes such as Ascaridia, e.g. Ascaridia galli, Trichostrongylidae, e.g. Nippostrongylus brasiliensis or Nematospiroides dubius, Ancylostomatidae, e.g. Necator americanus and Ancylostoma ceylanicum, and Strongylidae; against Cestoda such as Hymenolepsis nana, Anoplocephalidae and Taeniidae; and particularly against Trematoda such as Fasciolida, e.g. *Fasciola hepatica*, and especially Schistosoma, e.g. *Schistosoma mansoni, Schistosoma japonicum* and *Schistosoma hematobium*; also against the pathogens of filariasis, e.g. *Dipetalonema witei* and *Litomosoides carinii*. The anthelmintic preparations according to the invention can be used therefore for the treatment of warm-blooded animals in the case of infestation with parasitic helminthes such as the aforementioned, especially for the treatment of warm-blooded animals affected by schistosomiasis, hookworm infestation or filariasis.

The following Examples further illustrate the invention but in no way do they limit the scope thereof.

EXAMPLE 1

200 g of 4-(4-nitroanilino)-phenylisothiocyanate of a medium particle size of about 50 μm or less is mixed with 800 ml of a mixture of triglycerides of saturated fatty acids of the chain length $C_8 - C_{12}$, and the suspension is ground in a DYNO ® mill until the median of the particle size of the active ingredient is 1–3 μm. An addition is made of 5 g of glycerin monostearate to stabilise the suspension, and the volume is made up with the employed triglyceride to 1000 ml. The resulting suspension can be filled into gelatine capsules, in amounts of 0.50 ml and 0.75 ml, corresponding to 100 mg and 150 mg, respectively, of active ingredient, or, after the addition of flavouring substances, in amounts of, e.g., 2.5 ml and 5.0 ml, corresponding to 500 mg and 1000 mg, respectively, of active ingredient; or, for individual needs, the suspensions can also be administered dropwise.

EXAMPLE 2

To produce 10,000 tablets each containing 500 mg of active ingredient, 5.0 kg of 4-(4-nitroanilino)-phenylisothiocyanate is mixed with agglutinated wheat starch obtained by agglutination of 0.55 kg of wheat starch with about 1.3 kg of demineralised water, and the mixture is uniformly moistened with a further 0.5 kg of demineralised water; it is then kneaded into the form of a slightly plastic mass and subsequently pressed through a sieve having a mesh size of about 3 mm. The granulate is afterwards dried and again put through a sieve. To the dry granulate, the granular size of which has been made uniform, there are added 50 g of magnesium stearate, 30 g of talcum and 270 g of maize starch, 30 g of colloidal silicon dioxide, 900 g of a mixture of microcrystalline cellulose and carboxymethylcellulose, e.g. Avicel ®, FMC Corp., American Viscose Division, and 100 g of sodium lauryl sulphate. The resulting mixture is pressed into the form of tablets.

4-(4-nitroanilino)-phenylisothiocyanate is used in the form of the ground substance having a median of particle size of at most 10 μm, especially of at most 5 μm, for example 4.23 μm.

EXAMPLE 3

To produce 10.0 liters of a 10% aqueous suspension, 1.0 kg of 4-(4-nitroanilino)-phenylisothiocyanate, ground in a counter-jet mill until the median of the particle size is about 10 μm, is suspended in a solution of 300 g of sodium carboxymethylcellulose, 20 g of sodium lauryl sulphate, 60 g of a mixture of the sodium salts of p-hydroxybenzoic acid methyl ester and p-hydroxybenzoic acid propyl ester in 5.0 kg of demineralised water; and the suspension is made up to the desired volume of 10.0 liters. To the aqueous suspension there can also be added saccharin sodium, sugar and/or sorbitol, as well as the customary flavouring substances. The suspension can be measured out in the way that a syrup is by means of a measuring vessel or teaspoon, or for individual dosage requirements it can be measured out dropwise.

It is also possible to further grind the active ingredient ground in a counter-jet mill, or another pre-ground active ingredient, together with 5.0 kg of demineralised water containing 30 g of sodium lauryl sulphate, in a stirrer ball mill, e.g. in a Dyno ® mill, to give a median of particle size of about 5 μm; to subsequently add the remaining substances mentioned above; and to then make up the suspension to 10.0 liters.

EXAMPLE 4

5.0 g of 4(4-nitroanilino)-phenylisothiocyanate having a median of particle size of 4.23 μm is physically mixed under normal room conditions for 5 minutes with 45.0 g of maize starch. The mixing apparatus employed is a high-speed mixer having a propeller-like, sharp-edged stirring mechanism and a rotary speed of at least 15,000 r.p.m. There is obtained a homogeneous mixture having the properties described hereinbefore, cp. Table II.

The resulting powder mixture, as such or filled into capsules or suspended in an aqueous medium, can be administered perorally in dosages adapted to individual needs.

What we claim is:

1. An anthelminthic preparation for oral or rectal administration to warm-blooded animals, which preparations contain an anthelmintically effective amount of 4-(4-nitroanilino)-phenylisothiocyanate in solid form having a median of particle size of at most 10 μm in combination with a starch or in suspension in a member selected from the group consisting of water and triglycerides of $C_8$–$C_{22}$ fatty acids.

2. The anthelmintic preparation according to claim 1, wherein the solid 4-(4-nitroanilino)-phenylisothiocyanate has a median of particle size of at most 5 μm.

3. The anthelmintic preparation according to claim 1, which contains the solid 4-(4-nitroanilino)-phenylisothiocyanate in combination with a starch selected from the groups consisting of maize starch, wheat starch, potato starch and rice starch.

4. The anthelmintic preparation according to claim 3, which contains 1 part of the solid 4-(4-nitroanilino)-phenylisothiocyanate and 4 to 20 parts of the starch.

5. The anthelmintic preparation according to claim 4, which contains the solid 4-(4-nitroanilino)-phenylisothiocyanate in combination with maize starch.

6. The anthelmintic preparation according to claim 3, which contains the solid 4-(4-nitroanilino)-phenylisothiocyanate in combination with maize starch, which mixture is obtained by mixing in a high-speed mixer having a propeller-like sharp-edged stirring device.

7. The anthelmintic preparation according to claim 1, which contains the solid 4-(4-nitroanilino)-phenylisothiocyanate in the form of a suspension in water.

8. The anthelmintic preparation according to claim 1, which contains the solid 4-(4-nitroanilino)-phenylisothiocyanate in the form of a suspension in one or more triglycerides of $C_8$–$C_{22}$ fatty acids.

9. The anthelmintic preparation according to claim 1, which contains the solid 4-(4-nitroanilino)-phenylisothiocyanate in the form of a suspension in one or more triglycerides of $C_8$–$C_{12}$ saturated fatty acids.

10. The anthelmintic preparation according to claim 9 in which, the solid 4-(4-nitroanilino)-phenylisothiocyanate has a median of particle size of at most 5 μm.

11. The anthelmintic preparation according to claim 10, which contains 10–30% of 4-(4-nitroanilino)-phenylisothiocyanate.

12. The anthelmintic preparation according to claim 11, which contains about 20% of 4-(4-nitroanilino)-phenylisothiocyanate.

13. A method for the treatment of an infection caused by parasitic helminthes in a warm-blooded animal comprising administration to said animal of an amount of a preparation according to claim 1 which contains an anthelminthically effective dose of 4-(4-nitroanilino)-phenylisothiocyanate.

14. A method for the treatment of an infection caused by parasitic helminthes in a warm-blooded animal comprising administration on the same day to said animal of an amount of a preparation according to claim 1 which contains a dose of 4-(4-nitroanilino)-phenylisothiocyanate sufficient to cure said animal of the infection caused by the parasitic helminthes.

15. A method for the treatment of an infection caused by parasitic helminthes in a warm-blooded animal comprising administration on the same day to said animal of several partial amounts of a preparation according to claim 1 which together contain a dose of 4-(4-nitroanilino)-phenylisothiocyanate sufficient to cure said animal of the infection caused by the parasitic helminthes.

16. The method according to claim 13 for the treatment of warm-blooded animals affected by schistosomiasis.

17. The method according to claim 13 for the treatment of warm-blooded animals affected by hookworm infestation.

18. The method according to claim 13 for the treatment of warm-blooded animals affected by filariasis.

* * * * *